(12) United States Patent
Jeon et al.

(10) Patent No.: US 10,213,437 B2
(45) Date of Patent: Feb. 26, 2019

(54) PHARMACEUTICAL PREPARATION FOR MASKED TASTE ORAL ADMINISTRATION, CONTAINING CLOMIPRAMINE

(71) Applicant: CTC BIO, INC., Seoul (KR)

(72) Inventors: Hong Ryeol Jeon, Gyeonggi-do (KR); Do-Woo Kwon, Chungcheongnam-do (KR); Bong-Sang Lee, Gyeonggi-do (KR); Su-Jun Park, Gyeonggi-do (KR); Jiyeong Han, Ulsan (KR); Myeongcheol Kil, Jeollabuk-do (KR); Min Seop Kim, Seoul (KR)

(73) Assignee: CTC BIO, INC., Seoul (KR)

( * ) Notice: Subject to any disclaimer, the term of this patent is extended or adjusted under 35 U.S.C. 154(b) by 0 days.

(21) Appl. No.: 15/309,620

(22) PCT Filed: May 8, 2015

(86) PCT No.: PCT/KR2015/004660
§ 371 (c)(1),
(2) Date: Nov. 8, 2016

(87) PCT Pub. No.: WO2015/170939
PCT Pub. Date: Nov. 12, 2015

(65) Prior Publication Data
US 2017/0151254 A1 Jun. 1, 2017

(30) Foreign Application Priority Data

May 8, 2014 (KR) .......................... 10-2014-0054970
May 8, 2015 (KR) .......................... 10-2015-0064918

(51) Int. Cl.
| | | |
|---|---|---|
| A61K 31/55 | (2006.01) |
| A61K 47/32 | (2006.01) |
| A61K 47/36 | (2006.01) |
| A61K 9/00 | (2006.01) |
| A61K 9/70 | (2006.01) |
| A61K 9/16 | (2006.01) |
| A61K 9/20 | (2006.01) |

(52) U.S. Cl.
CPC .............. *A61K 31/55* (2013.01); *A61K 9/006* (2013.01); *A61K 9/0053* (2013.01); *A61K 9/1635* (2013.01); *A61K 9/1652* (2013.01); *A61K 9/205* (2013.01); *A61K 9/2027* (2013.01); *A61K 9/7007* (2013.01); *A61K 47/32* (2013.01); *A61K 47/36* (2013.01)

(58) Field of Classification Search
CPC ........ A61K 31/55; A61K 47/32; A61K 47/36; A61K 9/0053; A61K 9/006; A61K 9/1635; A61K 9/1652; A61K 9/2027; A61K 9/205; A61K 9/7007
See application file for complete search history.

(56) References Cited

U.S. PATENT DOCUMENTS

| | | | |
|---|---|---|---|
| 3,665,073 A | 5/1972 | Marshall et al. ............... 424/79 |
| 5,643,560 A * | 7/1997 | Bergwitz-Larsen ......................... A61K 47/585 424/78.11 |
| 2002/0098227 A1 | 7/2002 | Nouri et al. ................... 424/439 |
| 2010/0215740 A1* | 8/2010 | Pilgaonkar ........... A61K 9/0056 424/465 |
| 2011/0300224 A1* | 12/2011 | Murpani .............. A61K 9/0056 424/495 |

FOREIGN PATENT DOCUMENTS

| | | | | |
|---|---|---|---|---|
| EP | 2 583 669 | 4/2013 | .............. A61K 9/00 |
| KR | 10-2002-0015062 | 2/2002 | .............. A61K 9/20 |
| KR | 10-1082802 | 11/2011 | .............. A61K 31/55 |
| KR | 10-2014-0029435 | 3/2014 | |
| WO | WO 93/07860 | 4/1993 | .............. A61K 9/18 |
| WO | WO 02/41883 | 5/2002 | .............. A61K 31/00 |
| WO | WO 2012/136816 | 10/2012 | .............. A61K 9/20 |
| WO | WO 2013/027932 F | 2/2013 | .............. A61K 31/55 |
| WO | WO 2013/124818 | 8/2013 | .............. A61K 9/00 |

OTHER PUBLICATIONS

Schiffman et al. (Pharmacology Biochemistry and Behaviror, 65, 4, 599-609, 2000).*
Ham, W.S., et al., (2008). "Recent concepts of premature ejaculation". *Korean Journal of Urology*, 49(9):765-774.
International Search Report (ISR) dated Jul. 27, 2015 in PCT/KR2015/004660 published as WO 2015/170939.

* cited by examiner

*Primary Examiner* — Umamaheswari Ramachandran
(74) *Attorney, Agent, or Firm* — Harness, Dickey & Pierce, P.L.C.

(57) ABSTRACT

The present invention relates to a pharmaceutical preparation for oral administration comprising, as an active ingredient, clomipramine or a pharmaceutically acceptable salt thereof; and a cation exchange resin and an anion polymer as a taste masking agent, wherein the pharmaceutical preparation can be orally administered even while comprising a pharmaceutically effective amount of clomipramine because the unique tastes of clomipramine, particularly, all of the bitter taste, spicy taste and burning taste are effectively masked, and thus the convenience of drug intake and portability is improved, and a method for manufacturing thereof.

8 Claims, No Drawings

PHARMACEUTICAL PREPARATION FOR MASKED TASTE ORAL ADMINISTRATION, CONTAINING CLOMIPRAMINE

CROSS-REFERENCE TO RELATED APPLICATIONS

This application is a national phase application of PCT Application No. PCT/KR2015/004660, filed on 8 May 2015, which claims benefit of Korean Patent Application No. KR 10-2015-0064918 filed 8 May 2015 and Korean Patent Application No. KR 10-2014-0054970 filed 8 May 2014. The entire disclosures of the applications identified in this paragraph are incorporated herein by references.

FIELD

The present disclosure relates to a pharmaceutical preparation comprising clomipramine or a pharmaceutically acceptable salt thereof as an active ingredient. More specifically, a pharmaceutical preparation for oral administration comprising clomipramine or a pharmaceutically acceptable salt thereof as an active ingredient, wherein the pharmaceutical preparation can be orally administered even while comprising a pharmaceutically effective amount of clomipramine because the unique tastes of clomipramine, particularly, all of the bitter taste, spicy taste and burning taste are effectively masked, and thus the convenience of drug intake and portability is guaranteed, and a method for manufacturing thereof.

BACKGROUND

Clomipramine is a kind of a selective serotonin reuptake inhibitor (SSRI).

The clomipramine is a representative tricyclic antidepressant (TCA), and used as a therapeutic agent for premature ejaculation (Product Name: Anafranil). Diagnostic criteria of the premature ejaculation is DSM-IV-TR (Diagnostic and Statistical Manual of Mental Disorders, Fourth Edition, Text Revision), and according to this definition, the premature ejaculation refers to a case of persistent or recurrent ejaculation with minimal sexual stimulation before, on, or shortly after penetration.

The clomipramine can be administered into blood, but when considering the case of using a therapeutic agent for premature ejaculation and/or an antidepressant, and convenience of drug intake and portability due to characteristics of disease, oral formulation is preferred. Further, tablets containing clomipramine hydrochloride of 10 mg, 15 mg, 25 mg, 50 mg or 75 mg are commercially available, and it is reported that low dose has very little therapeutic effect like a placebo. For example, because it is recommended to administer the clomipramine hydrochloride of 250 mg per day for effective treatment for obsession, unit dose is large. However, because the clomipramine hydrochloride has a unique bitter taste together with a spicy taste, an burning taste and the like, there are problems of giving an unpleasant feeling when administered orally, causing local paralysis in the mouth in a severe case and the like. Thus, it is difficult to manufacture it in the formulation for oral administration, in particular, orally dispersible formulation whose taste is directly felt when orally administered, for example, orally disintegrating film, orally disintegrating table, suspension, dispersible tablet, fast-acting disintegrating tablet, orally disintegrating capsule, orally disintegrating granule, orally disintegrating troche, sublingual tablet, powder and/or chewable tablet.

More specifically, the reasons why the formulation for oral administration comprising the clomipramine hydrochloride as an active ingredient is limited are as follows.

There are many difficulties to manufacture the clomipramine hydrochloride in the formulation for oral administration because it has strong spicy taste and burning taste with a unique bitter taste and also has a symptom of tongue paralysis and the like.

Accordingly, first, in order to make taste masking (TM) of a unique taste due to the clomipramine hydrochloride and prediction of absorption pattern (for example, Cmax, Tmax) possible, a large amount of a taste masking agent and a large coating amount should be needed, and as a result, there is no choice but to increase a loading weight in a formulation Second, or, in order to load a large amount of the TM agent in a formulation having limited size, the amount of the clomipramine hydrochloride and other additives to be added is limited. Thus, in this case, it is difficult to manufacture a formulation having satisfactory activity, physical properties and a handling property.

Third, in order to manufacture the clomipramine hydrochloride in the film formulation, it is necessary to use a polymer in a certain amount or more for maintaining film shape. However, in order to load a large amount of a taste masking agent and a large coating amount in a film having limited size, the amount of the polymer should be highly decreased. If the amount of the polymer is not enough, it is difficult to have proper physical properties to handle the formed film (for example, flexibility, tensile force).

Finally, the largest problem is that it is difficult to completely mask all unpleasant tastes because the burning taste can't be masked even if the unique bitter taste and spicy taste can be masked by using a taste masking TM agent commonly used for taste masking of a pharmaceutical preparation.

DISCLOSURE

Technical Problem

The present disclosure is designed to solve the problems of the related art, and therefore the present disclosure is directed to providing a pharmaceutical preparation for oral administration, which is effective for oral administration by effectively masking all unique unpleasant tastes of clomipramine hydrochloride with a small amount, and a method for manufacturing thereof.

These and other objects and advantages of the present disclosure may be understood from the following detailed description and will become more fully apparent from the exemplary embodiments of the present disclosure. Also, it will be easily understood that the objects and advantages of the present disclosure may be realized by the means shown in the appended claims and combinations thereof.

Technical Solution

In one aspect of the present disclosure, there is provided a pharmaceutical preparation for oral administration comprising clomipramine or a pharmaceutically acceptable salt thereof as an active ingredient, and a cation exchange resin and an anion polymer together as a taste masking agent, and a method for manufacturing thereof.

More specifically, in one aspect, the present invention provides a pharmaceutical preparation for oral administration comprising clomipramine or a pharmaceutically acceptable salt thereof as an active ingredient, and a cation exchange resin and an anion polymer together as a taste masking agent.

The present inventors completed the present invention after found that if a cation exchange resin and an anion polymer are combined, unique tastes of clomipramine (particularly, clomipramine hydrochloride) can be very effectively masked with only small amount due to its synergy effect.

The pharmaceutical preparation according to the present invention can comprise a clomipramine derivative as an active ingredient, instead of or together with the clomipramine. Thus, the pharmaceutical preparation according to the present invention can comprise a derivative having the identical pharmaceutical activity with the clomipramine.

In the present invention, the 'clomipramine' includes a free base or a pharmaceutically acceptable salt.

In the present invention, the 'pharmaceutically acceptable salt' refers to any organic or inorganic additional salt, which is used in such a concentration that exhibits relatively non-toxic and harmless effective actions to a patient, and which has side effects that do not decrease advantageous effects of the base compound, and for example, it may use organic acid or inorganic acid as free acid or non-toxic salts. The inorganic acid may be hydrochloric acid, phosphoric acid, sulfuric acid, nitric acid, tartaric acid and the like, and the organic acid may be methane sulfonic acid, p-toluene sulfonic acid, acetic acid, trifluoroacetic acid, maleic acid, succinic acid, oxalic acid, benzoic acid, tartaric acid, fumaric acid, mandelic acid, propionic acid, citric acid, lactic acid, glycolic acid, gluconic acid, galacturonic acid, glutamic acid, glutaric acid, glucuronic acid, aspartic acid, ascorbic acid, carboxylic acid, vanillic acid, hydroiodic acid and the like, and preferably, it may be hydrochloric acid. The acid additional salt can be manufactured by a conventional method, for example, it can be manufactured by dissolving the compound in an excessive amount of aqueous acid solution and then precipitating the salt by using a water-miscible organic solvent, for example, methanol, ethanol, acetone or acetonitrile. Also, it can be manufactured by drying with evaporation of the same molar amount of a compound and an acid in water or alcohol or filtering the precipitated salt. In addition, equimolar amounts of the compound and an acid or alcohol in the water are heated, and then the mixture is dried by evaporation or the precipitated salt may be suction filtered. The non-toxic salts may be sulfate, pyrosulfate, bisulfate, sulfite, bisulfite, nitrate, phosphate, monohydrogen phosphate, dihydrogen phosphate, metaphosphate, pyrophosphate chloride, bromide, iodide, fluoride, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexane-1,6-dioate, benzoate, chlorobenzoate, methylbenzoate, dinitrobenzoate, hydroxybenzoate, methoxybenzophthalate, terephathalate, benzenesulfonate, toluenesulfonate, chlorobenzenesulfonate, xylenesulfonate, phenylacetate, phenylpropionate, phenylbutyrate, citrate, lactate, β-hydroxybutyrate, glycolate, malate, tartrate, methanesulfonate, propanesulfonate, naphthalene-1-sulfonate, naphthalene-2-sulfonate, or mandelate.

The 'cation exchange resin' may be anything if it does not have a negative impact on pharmaceutical activity of the clomipramine or a pharmaceutically acceptable salt thereof, without limitation, and it may be both of polyacryl-type and polystyrene-type. For example, it may be a cross-linked polymer of methacylic acid and divinylbenzene (carboxylic acid functional group of methacyclic acid and potassium form a weak acidic salt) (e.g., C100HMR®, C108DR®, C115HMR®, C115KMR®, IRP64®, IRP88®, INDION204®, INDION214®, INDION234®, INDION234S®, INDION264®, INDION414®, INDION464® or INDION294® (polacrylin potassium), cross-linked polymer of styrene sulfonic acid and divinylbenzene (sulfonic acid group of styrene and sodium form a strong acidic salt) (e.g., IRP69®, INDION224®, INDION254®, INDION404®, INDION284®), or cross-linked polymer of styrene and divinylbenzene (e.g., AP143/1083®, INDION244®) and the like, but not limited thereto.

The 'anion polymer' may be anything if it does not have a negative impact on pharmaceutical activity of the clomipramine or a pharmaceutically acceptable salt thereof, without limitation, and it includes both of a natural anion polymer and a synthetic anion polymer, for example, it may include, as a polymer having a functional group of alginic acid, carboxylic acid, sulfonic acid, sulfate ester, phosphate ester, phosphonic acid and its salts, pectin and its derivatives and salts, cellulose (e.g., carboxymethylcellulose (CMC)) and its derivatives and salts, polyacrylic acid acid (e.g., Eudragit®) and its derivatives and salts, galactomannan gums (e.g., cassia gum, locust bean gum, tara gum, guar gum), carrageenan gum, xanthan gum, gum tragacanth, agar, Queens seed gum, starch and its derivatives and salts, gum karaya, gum arabic, alginate (e.g., sodium alginate, propyleneglycol alginate) and derivatives and salts thereof, chondroitin sulfate, dextran sulfate, fucoidan, gellan gum, heparin, hyaluronic acid, xylan, polystyrene sulfonate, collagen, polyphosphoric acid, polyphosphates, poly(lactide) and poly(lactide-co-glycolic acid) and the like, but not limited thereto.

In order to exert a synergic effect of the cation exchange resin and the anion polymer as a taste masking agent, preferably, weight ratio of the anionic polymer to the cation exchange resin may be about 1:0.07 to 23, about 1:0.0.07 to 22, about 1:0.07 to 21, about 1:0.07 to 20, about 1:0.07 to 19, about 1:0.08 to 23, about 1:0.0.08 to 22, about 1:0.09 to 21, about 1:0.1 to 20, or about 9:1 to 1:19. If weight ratio is about less than 1:0.07 or about more than 1:23, it may difficult to exert a taste masking effect.

Because just combination of the cation exchange resin and the anion polymer can effectively mask all unpleasant tastes of the clomipramine with only small amount, total weight ratio of the cation exchange resin and the anion polymer as a taste masking agent, based on the clomipramine or a pharmaceutically acceptable salt thereof, may preferably be about 1:0.5 or more but less than 1:10, about 1:0.6 or more but less than 1:10, about 1:0.7 or more but less than 1:10, about 1:0.8 or more but less than 1:10, about 1:0.9 or more but less than 1:10, about 1:1 or more but less than 1:10, about 1:2 or more but less than 1:10, about 1:3 or more but less than 1:10, about 1:4 or more but less than 1:10, about 1:5 or more but less than 1:10, about 1:6 or more but less than 1:10, about 1:7 or more but less than 1:10, about 1:8 or more but less than 1:10, about 1:9 or more but less than 1:10. If weight ratio is about less than 1:0.5, it may difficult to exert taste masking effect, and if it is about 1:10 or more, texture in the mouth and intake convenience is significantly deteriorated due to increase of total weight, and there is high possibility that advantages of film formulation, in particular, portability may be cancelled out due to increase of size.

Preferably, the pharmaceutical preparation according to the present invention may include about 2-150 mg of the clomipramine or a pharmaceutically acceptable salt thereof per unit formulation, based on single unit dose. More specifically, depending on specific pharmaceutical use, single unit dose of the clomipramine or a pharmaceutically acceptable salt thereof contained in a pharmaceutical preparation may vary, but if combination of the cation exchange resin and the anion polymer as a taste masking agent is added within a range of about 2 to 250 mg of single unit dose of the clomipramine or a pharmaceutically acceptable salt thereof, unique tastes are effectively masked. Accordingly, for example, if all of the clomipramine or a pharmaceutically acceptable salt thereof corresponding to daily dose is contained in a unit formulation, the dose can be taken without repulsion. Thus, daily dose can be taken once without dividing the daily dose several times, it can be taken one time just before sex, and a treatment method can be changed from a consecutive treatment method taking a drug everyday to a periodical method taking a drug periodically with a certain dosage interval. Accordingly, it has effects of solving a problematic side effect of everyday consecutive treatment method and the like, but the present invention is not limited to these effects.

The pharmaceutical preparation according to the present invention can be used to any pharmaceutical use for all diseases, disorders and/or symptoms, which can be treated by administrating the clomipramine or a pharmaceutically acceptable salt thereof as an active ingredient, without limitation, and for example, it can be used for treating premature ejaculation, obsession, depressive disorder, panic disorder, body dysmorphic disorder, cataplexy, hypnolepsy, depersonalization, chronic pain, enuresis and/or trichotillomania, and symptoms resulted therefrom, and preferably, it can be used for treating premature ejaculation.

In the present invention, 'treatment' means all activities improving or beneficially changing diseases, disorders and symptoms resulted therefrom by administrating a pharmaceutical preparation. Further, because the 'treatment' broadly includes a meaning of 'prevention', the 'prevention' means all activities inhibiting diseases and symptoms resulted therefrom or delaying onset by administrating a pharmaceutical preparation.

The pharmaceutical preparation according to the present invention can be formulated for oral administration, and for example, it can be formulated as various forms such as tablet, film, suspension, granule, gel, pill, tincture, decoction, infusion, spirit, fluidextract, elixir, extract, syrup, powder, aromatic water and lemonade. Further, the tablet can be formulated as various forms such as, for example, orally disintegrating tablet, mucoadhesive tablet, dispersible tablet, sublingual tablet, buccal tablet, chewable tablet, dispensing tablet, mulita-layered tablet, press-coated tablet, forming tablet (effervescent tablet) and solution tablet. And those skilled in the art can use the various tablets by diversely changing thereof as needed. More preferably, like a liquid form or a formulation disintegrated in the mouth (i.e., disintegrability in the mouth), the tablet may be a formulation, which can immediately feel the unique tastes of the clomipramine when it is orally administered, for example, orally dispersible formulation, for example, orally disintegrating film, orally integrating tablet, suspension, suspension tablet, fast-acting disintegrating tablet, orally disintegrating granule, orally disintegrating troche, sublingual tablet, powder and/or chewable tablet. Considering many purposes such as taste masking as well as conditions administering a pharmaceutical preparation or portability, formulation of the pharmaceutical preparation according to the present invention may preferably be orally disintegrating film, fast-acting disintegrating table or orally disintegrating granule. The orally disintegrating film can be used interchangeably with terms such as film, strip, orally disintegrating film, and it means a formulation taken by attaching and dissolving it in the mouth such as on the tongue, on the oral mucosa and under the tongue. The pharmaceutical preparation for oral administration of orally disintegrating film according to the present invention has an advantage that it can be taken without water.

In the case that the pharmaceutical preparation according to the present invention for oral administration is formulated into orally disintegrating film, in the present invention, a polymer should be included for forming film. Because the pharmaceutical preparation according to the present invention for oral administration contains a large amount of ionic ingredients, interchangeability with a polymer is important. Thus, preferably, pullulan, hydroxypropylcellulose (HPC), hydroxypropyl methylcellulose (HPMC), polyvinylpyrrolidone (PVP), starch, polyethyeneglycol-polyvinylalcohol copolymer, co-povidone, hydroxyethylcellulose, hydroxypropyl p-starch, polyvinylcaprolactam-polyvinylacetate-polyethyleneglycol copolymer, poloxamer or a mixture thereof may be used. The polymer may be contained in an amount of 10 to 50 wt % based on the total weight of dried film, but not limited thereto.

When manufacturing the pharmaceutical preparation according to the present invention for oral administration, a pharmaceutically acceptable carrier, which can be added commonly to a pharmaceutical preparation, may be further contained. The pharmaceutically acceptable carrier may include additives commonly used in the pharmacology field such as a diluent, a disintegrant, a binder, a lubricant, an emulsifier, a suspending agent and a stabilizing agent, and as needed, a sweeting agent, a fragrance and/or a coloring agent can be added additionally.

In the present invention, if the pharmaceutical composition is used for treating premature ejaculation, as an active ingredient, drugs other than the clomipramine or a pharmaceutically acceptable salt thereof can be additionally used, unless the purposes of the present invention are not hindered, and for example, at least one selected from the group consisting of serotonin agonist, serotonin antagonist, adrenaline agonist, adrenaline antagonist, adrenergic neuron blocker, erectile-dysfunction drug, PDE 5-inhibitor, erection inducing agent and a combination thereof can be contained additionally. Other than the mentioned drugs, those skilled in the art can additionally choose many drugs as needed.

In another aspect, the present invention provides a method for manufacturing a pharmaceutical preparation for oral administration comprising clomipramine or a pharmaceutically acceptable salt thereof as an active ingredient, and a cation exchange resin and an anion polymer together as a taste masking agent.

Preferably, if the pharmaceutical preparation for oral administration is manufactured by a method comprising a step of adding the cation exchange resin and the anion polymer to liquid melt of clomipramine hydrochloride and then stirring thereof, the present invention can provide a method for manufacturing a pharmaceutical preparation for oral administration, which comprises clomipramine hydrochloride as an active ingredient and can be taken without water.

Advantageous Effects

The present disclosure gives the following effects.

The present invention can provide a pharmaceutical preparation for oral administration having excellent taste masking effect by comprising a step of adding a mixture of a cation exchange resin and an anion polymer to clomipramine or a pharmaceutically acceptable salt thereof in a solvent and then reacting thereof.

BEST MODE

Hereinafter, preferred embodiments of the present disclosure will be described in detail with reference to the accompanying drawings. Prior to the description, it should be understood that the terms used in the specification and the appended claims should not be construed as limited to general and dictionary meanings, but interpreted based on the meanings and concepts corresponding to technical aspects of the present disclosure on the basis of the principle that the inventor is allowed to define terms appropriately for the best explanation. Therefore, the description proposed herein is just a preferable example for the purpose of illustrations only, not intended to limit the scope of the disclosure, so it should be understood that other equivalents and modifications could be made thereto without departing from the scope of the disclosure.

Test Example 1. Preparation of Film Formulation Comprising Clomipramine Hydrochloride as Active Ingredient Using the ingredients according to Table 2, a film formulation comprising clomipramine hydrochloride as an active ingredient as manufactured according to the following method, and taste masking effect and capability of forming the film formulation were checked.

A cation exchange resin and an anion polymer were added to a liquid melt of clomipramine hydrochloride and stirred for 1 hour or longer. Then, a plasticizer, a flavor, a coloring agent, a sweeting agent, a surfactant and/or a diluent was added to purified water, stirred for dissolving or dispersing thereof, and then homogenized by using a homogenizer (Ultra turrax T-25, IKA). A polymer (pullulan) was added thereto, homogenized again by using the same homogenizer. Gas in the manufactured film solution was removed under vacuum condition, and then the solution was coated on a PET film to have proper thickness. Then, it was dried at 60 to 80° C. to manufacture a film formulation comprising clomipramine hydrochloride.

Taste making effect of the film formulation was checked by the following method. TM sensory test was performed for the same amount of the manufactured formulations. A subject inserted a sample of the formulation comprising the same unit equivalent of clomipramine hydrochloride into his mouth, melted it for the same time period, spitted it out, and then lightly rinsed his mouth with the same amount of water. Then, time of retaining a bitter taste and burning effect was recorded, respectively. A distance of test time between formulations and between samples was set to 3 hour or longer, and if the bitter taste or the burning effect were retained for 3 hour or longer, the corresponding subject was excluded from the next test. Further, specific evaluation criteria were as follows:

TABLE 1

| | |
|---|---|
| 1 - poor | Retention time of Bitter, burning effects: NLT 60 min. |
| 2 - not good | Retention time of Bitter, burning effects: NLT 20 min. |
| 3 - not bad | Retention time of Bitter, burning effects: NMT 20 min. |
| 4 - excellent | Retention time of Bitter, burning effects: NMT 5 min. |

Further, Evaluation criteria for capability of forming film formulation were as follows:

Not formed: It is difficult for stirring and coating due to high viscosity of film solution.

Bad appearance: Viscosity of film solution is enough for stirring and coating, but structure of dried film is irregular and rough.

Not bad appearance: Stirring and coating of film solution are good, but structure of dried film is rough.

Excellent: Stirring and coating of film solution are excellent, and structure of dried film is uniform and flat.

The method of the present invention had an excellent effect that it is effectively possible to prevent release of the active pharmaceutical ingredient (API) while removing free API at the same time, even though not going through a filtering step, a washing step and/or a drying step. Thus, it had a taste making effect as well an effect of reducing time, cost, effort and the like in a manufacturing process.

TABLE 2

| | Comp. | Example | | | | | | | | | | | |
|---|---|---|---|---|---|---|---|---|---|---|---|---|---|
| | 1 | 2 | 3 | 4 | 5 | 6 | 7 | 8 | 9 | 10 | 11 | 12 | 13 |
| Clomipramine HCl | | | | | | | 4.30 | | | | | | |
| Carrageenan | — | 4.30 | 4.30 | 4.30 | — | — | — | — | — | — | — | — | — |
| Propylene glycol alginate | — | — | — | — | 4.30 | 4.30 | 4.30 | — | — | — | — | — | — |
| Xanthan gum | — | — | — | — | — | — | — | 4.30 | 4.30 | 4.30 | — | — | — |
| Methacrylic acid-ethyl acrylate | — | — | — | — | — | — | — | — | — | — | 4.30 | 4.30 | 4.30 |
| IRP64 | — | 4.30 | — | — | 4.30 | — | — | 4.30 | — | — | 4.30 | — | — |
| IRP69 | — | — | 4.30 | — | — | 4.30 | — | — | 4.30 | — | — | 4.30 | — |
| IRP88 | — | — | — | 4.30 | — | — | 4.30 | — | — | 4.30 | — | — | 4.30 |
| Pullulan | | | | | | | 12.9 | | | | | | |
| Glycerin | | | | | | | 2.3 | | | | | | |
| Diluent | | | | | | | 2.9 | | | | | | |
| Sucralose | | | | | | | 1.4 | | | | | | |
| Pigment | | | | | | | Q.S | | | | | | |
| flavor | | | | | | | Q.S | | | | | | |
| Water | | | | | | | to 100% | | | | | | |
| Taste masking value | 1 | 4 | 4 | 3 | 3 | 4 | 3 | 3 | 4 | 3 | 2 | 3 | 3 |
| Forming | 4 | 4 | 4 | 4 | 4 | 4 | 4 | 4 | 4 | 4 | 3 | 3 | 3 |

Test Example 1-1. Comparison of Effects According to Mixing Ratio of Cation Exchange Resin, Anion Polymer and Clomipramine Hydrochloride As shown in Table 3, film formulations were manufactured with different weight ratio of a cation exchange resin, an anion polymer and clomipramine hydrochloride, and taste masking effect and capability of forming film formulation were checked.

Manufacturing the film formulation and checking the effects of taste masking and capability of forming film formulation were performed identically as described in Test Example 1.

TABLE 3

| | Comp. | Example (Resin:anion-polymer) % | | | | | | | | | |
|---|---|---|---|---|---|---|---|---|---|---|---|
| | 1 | 2 | 3 | 4 | 5 | 6 | 7 | 8 | 9 | 10 | 11 |
| | — | 1:24 | 1:19 | 9:1 | 15.7:1 | 1:24 | 1:19 | 9:1 | 15.7:1 | 9:1 | 1:19 |
| API: (Resin:anion-polymer) | — | 1:0.5 | | | | 1:10 | | | | 1:3 | |
| Clomipramine HCl | | | | | | 4.30 | | | | | |
| IRP69 | — | 0.086 | 0.1075 | 1.935 | 2.021 | 1.720 | 2.150 | 38.700 | 40.420 | 11.61 | 0.645 |
| Carrageenan | — | 2.064 | 2.0425 | 0.215 | 0.129 | 41.28 | 40.85 | 4.30 | 2.58 | 1.29 | 12.255 |
| Pullulan | | | | | | 12.9 | | | | | |
| Glycerin | | | | | | 2.3 | | | | | |
| Diluent | | | | | | 2.9 | | | | | |
| Sucralose | | | | | | 1.4 | | | | | |
| Pigment | | | | | | Q.S | | | | | |
| flavor | | | | | | Q.S | | | | | |
| Water | | | | | | to 100% | | | | | |
| Taste masking value | 1 | 1 | 3 | 3 | 1 | 3 | 4 | 4 | 3 | 4 | 3 |
| Forming | 4 | 4 | 4 | 4 | 4 | 2 | 2 | 4 | 4 | 4 | 3 |

Test Example 2. Preparation of Fast-Acting Disintegrating Tablet Comprising Clomipramine Hydrochloride as Active Ingredient Using the ingredients according to Table 4, a tablet formulation comprising clomipramine hydrochloride as an active ingredient as manufactured according to the following method, and taste masking effect and capability of forming the film formulation were checked.

A cation exchange resin and an anion polymer were added to liquid melt of clomipramine hydrochloride and stirring thereof for 1 hour or longer.

Then, the solution was filtered and then dried to obtain solid. A binder, a disintegration agent, a diluent, a lubricant were added to the obtained solid and mixed, and then the mixture was tableted by using a tablet machine.

TABLE 4

| | Comp. | Example | | | | | | | | | | | |
|---|---|---|---|---|---|---|---|---|---|---|---|---|---|
| | 1 | 2 | 3 | 4 | 5 | 6 | 7 | 8 | 9 | 10 | 11 | 12 | 13 |
| Clomipramine HCl | | | | | | | 5.375 | | | | | | |
| Carrageenan | — | 5.375 | 5.375 | 5.375 | — | — | — | — | — | — | — | — | — |
| Propylene glycol alginate | — | — | — | — | 5.375 | 5.375 | 5.375 | — | — | — | — | — | — |
| Xanthan gum | — | — | — | — | — | — | — | 5.375 | 5.375 | 5.375 | — | — | — |
| Methacrylic acid-ethyl acrylate | — | — | — | — | — | — | — | — | — | — | 5.375 | 5.375 | 5.375 |
| IRP64 | — | 5.375 | — | — | 5.375 | — | — | 5.375 | — | — | 5.375 | — | — |
| IRP69 | — | — | 5.375 | — | — | 5.375 | — | — | 5.375 | — | — | 5.375 | — |
| IRP88 | — | — | — | 5.375 | — | — | 5.375 | — | — | 5.375 | — | — | 5.375 |
| Binder & Disintegration agent & Diluent | | | | | | | 68.8 | | | | | | |
| Sucralose | | | | | | | 1.4 | | | | | | |
| flavor (If needed) | | | | | | | Q.S | | | | | | |
| Lubricant (If needed) | | | | | | | Q.S | | | | | | |
| Water | | | | | | | to 100% | | | | | | |
| Taste masking value | 1 | 4 | 4 | 3 | 3 | 4 | 3 | 3 | 4 | 3 | 2 | 3 | 3 |
| Forming | — | — | — | — | — | — | — | — | — | — | — | — | — |

Test Example 2-1. Comparison of Effects According to Mixing Ratio of Cation Exchange Resin, Anion Polymer and Clomipramine Hydrochloride As shown in Table 5, tablets were manufactured with different weight ratio of a cation exchange resin, an anion polymer and clomipramine hydrochloride, and taste masking effect was checked.

Manufacturing the tablet and checking the taste masking effect were performed identically as described in Test Example 1.

TABLE 5

| | Comp. | Example (Resin:anion-polymer) % | | | | | | | | | |
|---|---|---|---|---|---|---|---|---|---|---|---|
| | 1 | 2 | 3 | 4 | 5 | 6 | 7 | 8 | 9 | 10 | 11 |
| | — | 1:24 | 1:19 | 9:1 | 15.7:1 | 1:24 | 1:19 | 9:1 | 15.7:1 | 9:1 | 1:19 |
| API: (Resin:anion-polymer) | — | 1:0.5 | | | | 1:10 | | | | 1:3 | |
| Clomipramine HCl | | | | | | 5.375 | | | | | |
| IRP69 | — | 0.108 | 0.1344 | 2.419 | 2.526 | 2.150 | 2.688 | 48.375 | 50.525 | 14.513 | 0.806 |
| Carrageenan | — | 2.580 | 2.5531 | 0.269 | 0.161 | 51.60 | 51.06 | 5.38 | 3.23 | 1.61 | 15.32 |
| Binder & Disintegration agent & Diluent | | | | | | 68.8 | | | | | |
| Sucralose | | | | | | 1.4 | | | | | |
| flavor (If needed) | | | | | | Q.S | | | | | |
| Lubricant (If needed) | | | | | | Q.S | | | | | |
| Water | | | | | | to 100% | | | | | |
| Taste masking value | 1 | 1 | 3 | 3 | 1 | 3 | 4 | 4 | 3 | 4 | 3 |
| Forming | — | — | — | — | — | — | — | — | — | — | — |

Test Example 3. Preparation of Granule Comprising Clomipramine Hydrochloride as Active Ingredient Using the ingredients according to Table 6, a granule formulation comprising clomipramine hydrochloride as an active ingredient as manufactured according to the following method, and taste masking effect and capability of forming the film formulation were checked.

A cation exchange resin and an anion polymer were added to liquid melt of clomipramine hydrochloride and stirring thereof for 1 hour or longer.

Then, the solution was filtered and then dried to obtain solid. Solution containing a binder, a disintegration agent and a diluent was prepared, and then the obtained solid was put into a fluidized bed granulator followed by spray-drying thereof to obtain granule.

TABLE 6

| | Comp. | Example | | | | | | | | | | | |
|---|---|---|---|---|---|---|---|---|---|---|---|---|---|
| | 1 | 2 | 3 | 4 | 5 | 6 | 7 | 8 | 9 | 10 | 11 | 12 | 13 |
| Clomipramine HCl | | | | | | | 5.375 | | | | | | |
| Carrageenan | — | 5.375 | 5.375 | 5.375 | — | — | — | — | — | — | — | — | — |
| Propylene glycol alginate | — | — | — | — | 5.375 | 5.375 | 5.375 | — | — | — | — | — | — |
| Xanthan gum | — | — | — | — | — | — | — | 5.375 | 5.375 | 5.375 | — | — | — |
| Methacrylic acid-ethyl acrylate | — | — | — | — | — | — | — | — | — | — | 5.375 | 5.375 | 5.375 |
| IRP64 | — | 5.375 | — | — | 5.375 | — | — | 5.375 | — | — | 5.375 | — | — |
| IRP69 | — | — | 5.375 | — | — | 5.375 | — | — | 5.375 | — | — | 5.375 | — |
| IRP88 | — | — | — | 5.375 | — | — | 5.375 | — | — | 5.375 | — | — | 5.375 |
| Binder & Disintegration agent & Diluent | | | | | | | 68.8 | | | | | | |
| Sucralose | | | | | | | 1.4 | | | | | | |
| flavor (If needed) | | | | | | | Q.S | | | | | | |
| Lubricant (If needed) | | | | | | | Q.S | | | | | | |
| Water | | | | | | | to 100% | | | | | | |
| Taste masking value | 1 | 4 | 4 | 3 | 3 | 4 | 3 | 3 | 4 | 3 | 2 | 3 | 3 |
| Forming | — | — | — | — | — | — | — | — | — | — | — | — | — |

Test Example 3-1. Comparison of Effects According to Mixing Ratio of Cation Exchange Resin, Anion Polymer and Clomipramine Hydrochloride As shown in Table 7, granules were manufactured with different weight ratio of a cation exchange resin, an anion polymer and clomipramine hydrochloride, and taste masking effect was checked.

Manufacturing the granule and checking the taste masking effect were performed identically as described in Test Example 1.

TABLE 7

| | Comp. 1 | Example (Resin:anion-polymer) % | | | | | | | | | |
|---|---|---|---|---|---|---|---|---|---|---|---|
| | | 2<br>1:24 | 3<br>1:19 | 4<br>9:1 | 5<br>15.7:1 | 6<br>1:24 | 7<br>1:19 | 8<br>9:1 | 9<br>15.7:1 | 10<br>9:1 | 11<br>1:19 |
| API: (Resin:anion-polymer) | — | 1:0.5 | | | | 1:10 | | | | 1:3 | |
| Clomipramine HCl | | | | | | 5.375 | | | | | |
| IRP69 | — | 0.108 | 0.1344 | 2.419 | 2.526 | 2.150 | 2.688 | 48.375 | 50.525 | 14.513 | 0.806 |
| Carrageenan | — | 2.580 | 2.5531 | 0.269 | 0.161 | 51.60 | 51.06 | 5.38 | 3.23 | 1.61 | 15.32 |
| Binder & Disintegration agent & Diluent | | | | | | 68.8 | | | | | |
| Sucralose | | | | | | 1.4 | | | | | |
| flavor (If needed) | | | | | | Q.S | | | | | |
| Lubricant (If needed) | | | | | | Q.S | | | | | |
| Water | | | | | | to 100% | | | | | |
| Taste masking value | 1 | 1 | 3 | 3 | 1 | 3 | 4 | 4 | 3 | 4 | 3 |
| Forming | — | — | — | — | — | — | — | — | — | — | — |

The present disclosure has been described in detail. However, it should be understood that the detailed description and specific examples, while indicating preferred embodiments of the disclosure, are given by way of illustration only, since various changes and modifications within the scope of the disclosure will become apparent to those skilled in the art from this detailed description.

What is claimed is:

1. A method for manufacturing a pharmaceutical preparation for oral administration comprising clomipramine as a sole active ingredient comprising:
    adding a cation exchange resin and an anion polymer to a liquid melt of clomipramine hydrochloride and stirring for at least 1 hour.
2. The method of claim 1, wherein the cation exchange resin is a polyacryl-type cation exchange resin, a polystyrene-type cation exchange resin, or a mixture thereof.
3. The method of claim 2, wherein the cation exchange resin is a cross-linked polymer of methacrylic acid and divinylbenzene, a cross-linked polymer of styrene sulfonic acid and divinylbenzene, or a mixture thereof.
4. The method of claim 1, wherein the anion polymer is an anionic gum, alginate, polyacrylic acid, or a mixture thereof.
5. The method of claim 4, wherein the anion polymer is selected from the group consisting of pectin and salts thereof, cellulose, cassia gum, locust bean gum, tara gum, guar gum, carraggenan gum, xanthan gum, gum tragacanth, agar, Queens seed gum, starch and salts thereof, gum karaya, gum Arabic, chondroitin sulfate, dextran sulfate, fucoidan, gellan gum, heparin, hyaluronic acid, xylan, polystyrene sulfonate, collagen, polyphosphoric acid, polyphosphate, poly(lactide) and poly(lactide-co-glycolic acid).
6. The method of claim 1, wherein a weight ratio of the anion polymer to the cation exchange resin is about 1:19 to about 9:1.
7. The method of claim 1, wherein a total weight ratio of the cation exchange resin and the anion polymer to the clomipramine HCl is from about 1:0.5 to 1:10.
8. The method of claim 1, wherein the pharmaceutical preparation for oral administration is an orally disintegrating film, a fast-acting disintegrating tablet, or an orally disintegrating granule.

* * * * *